US011253335B2

(12) United States Patent
Pathy et al.

(10) Patent No.: US 11,253,335 B2
(45) Date of Patent: Feb. 22, 2022

(54) LIGHTING DEVICES FOR ATTACHMENT TO A HANDHELD ELECTROSURGICAL INSTRUMENT

(71) Applicant: Pathy Medical, LLC, Shelton, CT (US)

(72) Inventors: Vinod V. Pathy, Shelton, CT (US); Mikiya Silver, New Haven, CT (US); Gennady Kleyman, Brooklyn, NY (US)

(73) Assignee: Pathy Medical, LLC, Shelton, CT (US)

( * ) Notice: Subject to any disclaimer, the term of this patent is extended or adjusted under 35 U.S.C. 154(b) by 142 days.

(21) Appl. No.: 16/653,065

(22) Filed: Oct. 15, 2019

(65) Prior Publication Data

US 2020/0121412 A1 Apr. 23, 2020

Related U.S. Application Data

(60) Provisional application No. 62/746,933, filed on Oct. 17, 2018.

(51) Int. Cl.
| | |
|---|---|
| *A61B 90/35* | (2016.01) |
| *F21V 21/088* | (2006.01) |
| *F21V 15/01* | (2006.01) |
| *F21V 19/00* | (2006.01) |
| *F21V 23/04* | (2006.01) |

(Continued)

(52) U.S. Cl.
CPC .......... *A61B 90/35* (2016.02); *A61B 18/1402* (2013.01); *F21V 5/04* (2013.01); *F21V 15/01* (2013.01); *F21V 19/0015* (2013.01); *F21V 21/088* (2013.01); *F21V 21/0808* (2013.01); *F21V 21/096* (2013.01); *F21V 23/04* (2013.01); *A61B 2017/00477* (2013.01); *A61B 2017/00734* (2013.01); *F21W 2131/205* (2013.01); *F21Y 2115/10* (2016.08)

(58) Field of Classification Search
CPC ................ A61B 90/35; A61B 18/1402; A61B 2017/00734; A61B 2017/00477; A61B 90/30; F21V 21/088; F21V 15/01; F21V 19/0015; F21V 33/0068; F21W 2131/205
See application file for complete search history.

(56) References Cited

U.S. PATENT DOCUMENTS 4,470,177 A * 9/1984 Ganung ................. A62C 33/04
                                                    24/270
5,199,947 A    4/1993 Lopez et al.
(Continued)

FOREIGN PATENT DOCUMENTS

KR    10-2013-0034068 A    4/2013

OTHER PUBLICATIONS

International Preliminary Report on Patentability and Written Opinion issued in corresponding PCT Patent Application No. PCT/US2019/056344, dated Apr. 14, 2021.

*Primary Examiner* — Tsion Tumebo
(74) *Attorney, Agent, or Firm* — Locke Lord LLP; Scott D. Wofsy

(57) ABSTRACT

A cordless, battery powered lighting device is disclosed which is configured to be removably installed on a distal end portion of a handheld electrosurgical instrument, and once the lighting device is installed on the distal end portion of the instrument, light automatically projects from the lighting device along the longitudinal axis of the surgical instrument.

17 Claims, 14 Drawing Sheets

(51) Int. Cl.
  *F21V 21/08* (2006.01)
  *F21V 21/096* (2006.01)
  *F21W 131/205* (2006.01)
  *A61B 17/00* (2006.01)
  *F21Y 115/10* (2016.01)
  *A61B 18/14* (2006.01)
  *F21V 5/04* (2006.01)

(56) References Cited

U.S. PATENT DOCUMENTS

| | | | | |
|---|---|---|---|---|
| 5,797,670 | A * | 8/1998 | Snoke | B25B 23/18 24/16 PB |
| 7,226,183 | B2 * | 6/2007 | Galli | F21V 21/084 362/110 |
| 8,496,475 | B2 * | 7/2013 | Jamnia | H02J 7/0044 433/29 |
| 8,746,264 | B2 * | 6/2014 | Gorey | A45B 3/04 135/66 |
| 9,651,228 | B2 * | 5/2017 | Wang | F21V 21/0885 |
| 9,759,524 | B2 * | 9/2017 | Culp | F41G 11/003 |
| 9,851,060 | B2 * | 12/2017 | Pathy | F21V 33/0068 |
| 9,907,565 | B2 * | 3/2018 | Aldridge | A61B 17/320068 |
| 10,194,975 | B1 * | 2/2019 | Hubelbank | F21V 29/70 |
| 10,401,001 | B2 * | 9/2019 | Kennedy | A61B 1/0684 |
| 2006/0271096 | A1 * | 11/2006 | Hamada | A61B 17/3439 606/198 |
| 2011/0176309 | A1 * | 7/2011 | Lin | F21L 4/04 362/249.02 |
| 2012/0283718 | A1 * | 11/2012 | Cosmescu | A61B 18/1402 606/33 |
| 2014/0293590 | A1 | 10/2014 | Pathy | |
| 2016/0278874 | A1 * | 9/2016 | Fleenor | A61B 18/1402 |
| 2017/0224335 | A1 * | 8/2017 | Weaner | A61B 17/068 |
| 2018/0318034 | A1 * | 11/2018 | Julian Ibanez | A61B 90/35 |
| 2020/0306001 | A1 * | 10/2020 | Silver | F21L 4/00 |

* cited by examiner

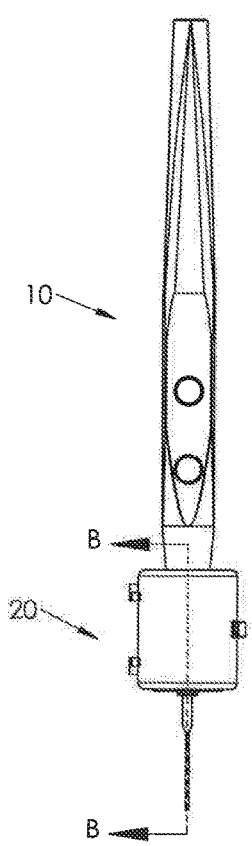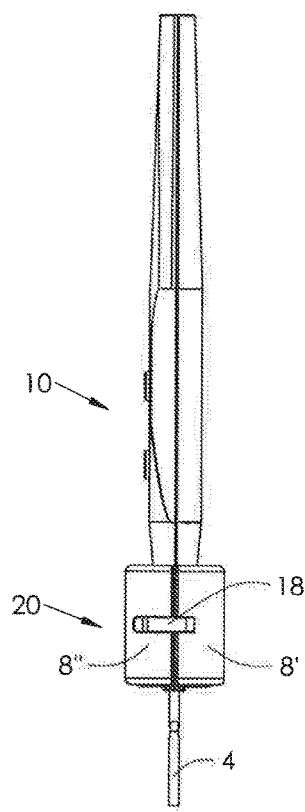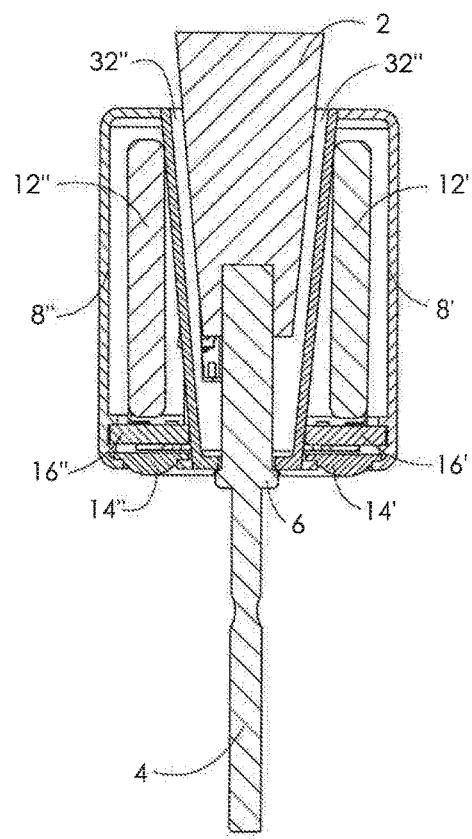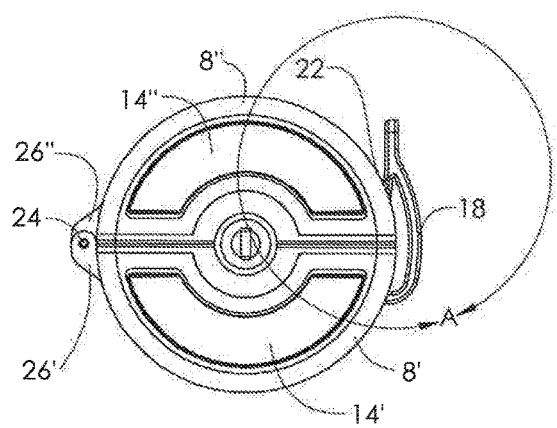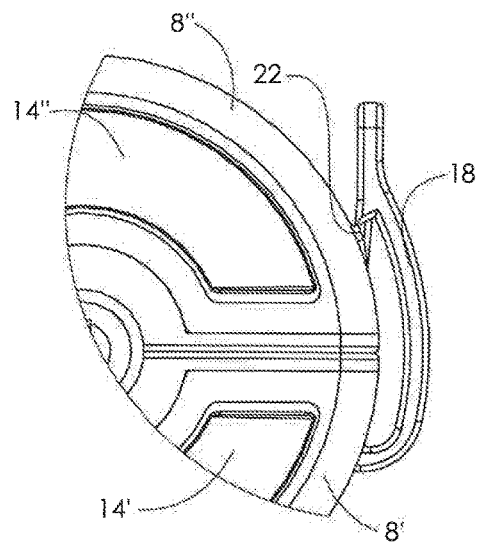
FIG. 3　　FIG. 4　　FIG. 5
FIG. 6　　FIG. 7

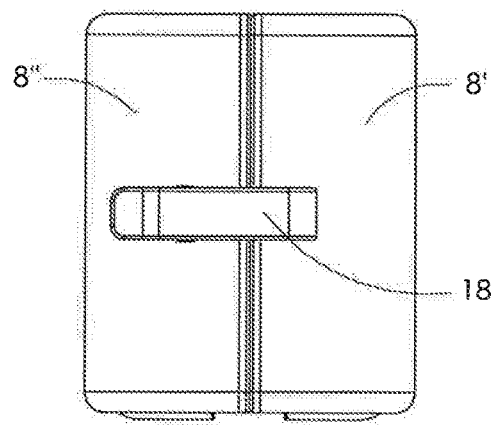
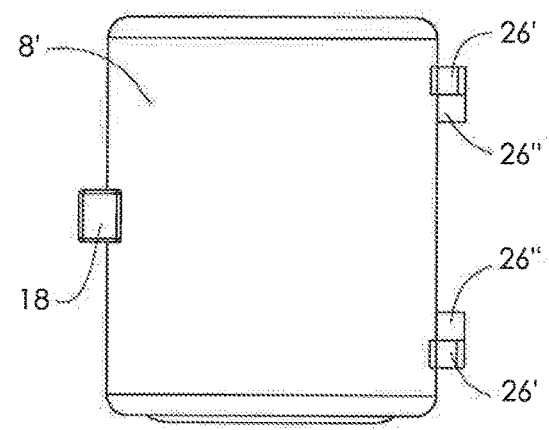
FIG. 8
FIG. 9
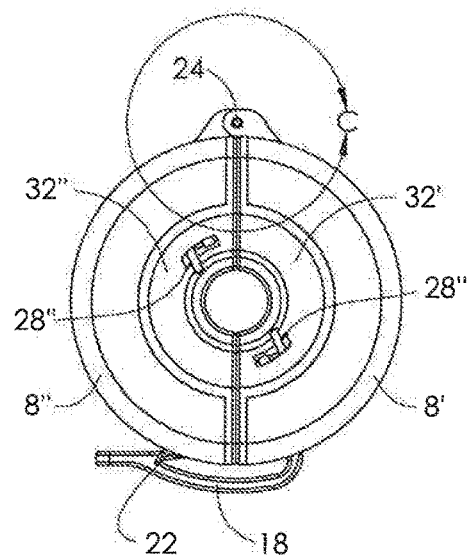
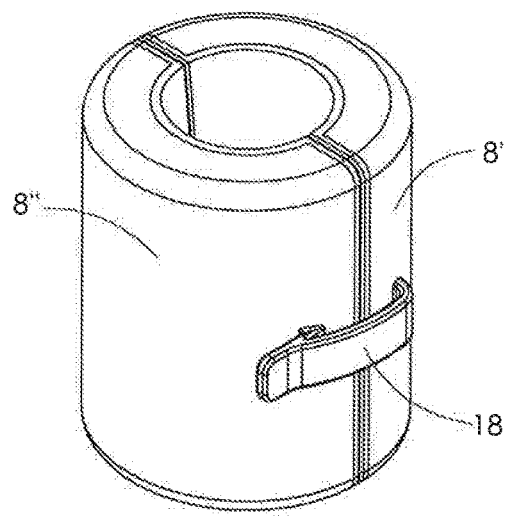
FIG. 10
FIG. 11

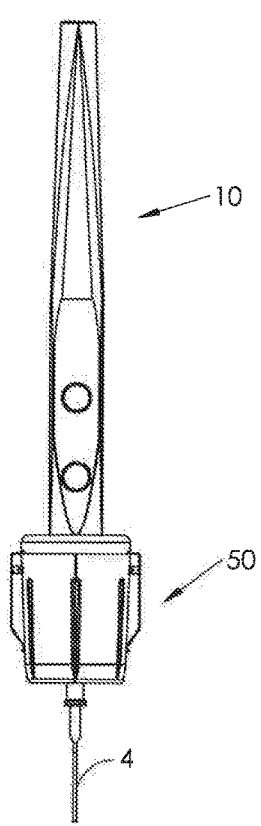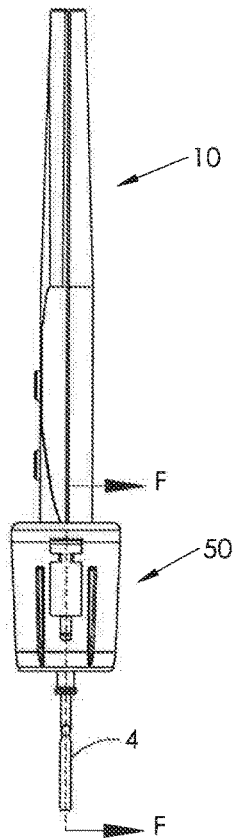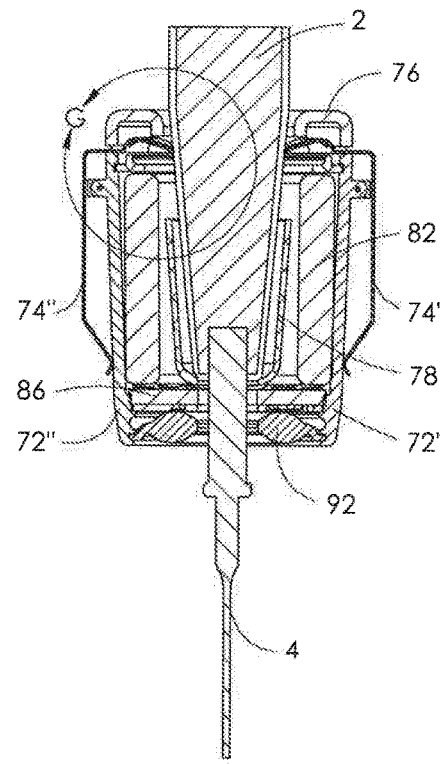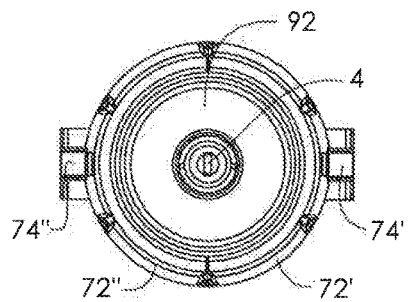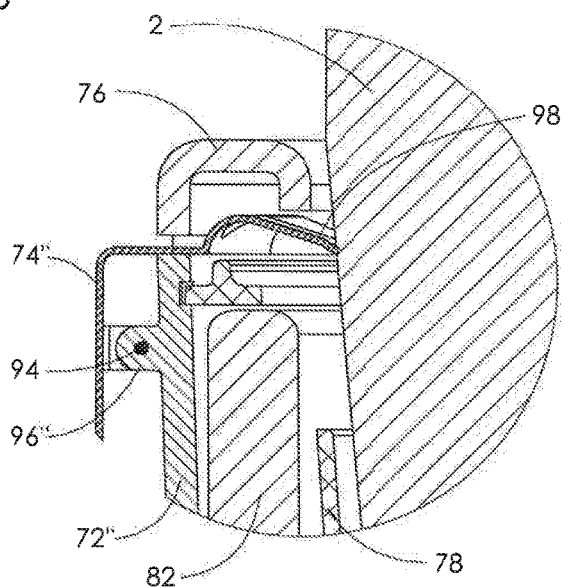
FIG. 42
FIG. 43
FIG. 44
FIG. 45
FIG. 46

LIGHTING DEVICES FOR ATTACHMENT TO A HANDHELD ELECTROSURGICAL INSTRUMENT

CROSS REFERENCE TO RELATED APPLICATIONS

This application claims the benefit of U.S. Provisional Patent Application No. 62/746,933, filed Oct. 17, 2018. The contents of this application are incorporated herein it its entirety.

BACKGROUND OF THE INVENTION

1. Field of the Invention

The subject invention is directed to surgical instrumentation, and more particularly, to battery powered lighting devices for attachment to handheld electrosurgical instruments.

2. Description of Related Art

Lighting devices are typically used to allow an operator to illuminate, and thus more precisely control and enhance, a space or area with a lighted field of view. In many situations, a lighting device can be used to illuminate a closed or confined space that would not regularly receive an adequate amount of light, if at all.

Existing lighting devices are connectable to a variety of tools, including, for example, medical devices and hand tools such as screwdrivers, to illuminate the area in which the device or tool is to be used. Such lighting devices and light sources include attachments that have an electrical cord extending therefrom that in turn is connectable to a power source, attachments that are battery powered, and light sources integrally formed within a tool to direct light on a specific field of view.

In medical practice, lighting devices are used to direct light at a specific area being operated on or examined. For example, lighting devices can be used in conjunction with electrosurgical handheld devices, such as an electrosurgical pencil like a BOVIE® pencil used to incise through tissues, and a variety of other operative instruments, such as retractors and forceps. Lighted retractors are commonly used during surgeries to help illuminate the surgical field.

The inventor has discerned a number of disadvantages of previously known lighting devices. For example, known lighting devices that include a light source integrally formed therein are generally expensive, bulky, and can cause injury. Known cordless and corded lighting devices add significant bulk to a tool preventing a user from manipulating the tool with the precision required in many situations and being able to extend the tool into tight spaces.

Additionally, many lighting devices, especially corded lighting devices and overhead lights, require constant repositioning, are cumbersome, are assistant-dependent to hold or re-position, and can be disruptive to a surgical field. Further, corded lighting devices as well as light sources integrally formed within a tool can become hot, burn the user and/or the patient, and possibly even cause a fire.

Headlights can be used as an alternative to a lighting device during a surgical procedure. However, similar to lighting devices, headlights are bulky, commonly require cables to connect to a power source, require constant readjustment, and can pose a potential safety hazard. In addition, headlamps are not sterile. Moreover, being worn on the head of the surgeon, they are at a distance from the surgical field, decreasing their effectiveness, and can be cumbersome to the user, and cause fatigue if worn for an extended period of time.

It is known that when handheld lighting devices, lighted retractors, overhead lights, and/or headlamps are employed during a surgical procedure, the hands/tools of the surgeon can block the light and cast a shadow on the surgical site, which is undesirable. Even the anatomy of the surgical cavity can block the light and cause shadows. Those shadows often require the user to reposition the lighting sources regularly, and can even require the surgeon to move their head to try to angle the headlamp towards the surgical site differently.

A particularly useful lighting device designed for attachment to a handheld electrosurgical device, and in particular, for use with a BOVIE® pen, is disclosed in commonly assigned U.S. Pat. No. 9,851,060, the disclosure of which is herein incorporated by reference in its entirety. The subject invention provides improvement to the lighting device disclosed therein.

SUMMARY OF THE DISCLOSURE

The subject invention is directed to new and useful lighting devices for installation on a handheld surgical instrument, and preferably, for releasable attachment to a handheld electrosurgical instrument.

Throughout the summary and detailed description of the invention that follows, reference is made to light emitting sources. These components may be comprised of light-emitting diodes, such as blue LEDs, white LEDs, yellow LEDs, etc. LEDs are advantageous because they consume less energy, have a longer lifetime, are available in smaller sizes, and provide faster switching than other types of lights. Nevertheless, other types of lights may also be used. For example, the light emitting sources could be adapted and configured to produce UV light, including UV-C light to treat or prophylax against infectious organisms.

In one embodiment of the subject invention, the lighting device includes a first outer body portion having a first interior body portion defining a first recess portion for accommodating a distal end portion of the surgical instrument. The first outer body portion has a first set of arcuately spaced apart light emitting source at a distal end thereof. The lighting device further includes a second outer body portion having a second interior body portion defining a second recess portion for accommodating the distal end portion of the surgical instrument. The second outer body portion has a second set of arcuately spaced apart light emitting source at a distal end thereof.

The first and second body portions of the lighting device are hingedly connected to one another and configured for movement between an open position for receiving the distal end portion of the surgical instrument and a closed positon for engaging the distal end portion of the surgical instrument. Preferably, the first and second outer body portions each have a generally hemi-cylindrical configuration, and the first and second recess portions each have a generally hemi-frusto-conical configuration. It is envisioned that the internal walls of the first and second recess portions could be formed from a flexible or resilient material so that the lighting device could accommodate a variety of surgical instruments of different size and/or geometry.

The first and second outer body portions each define a respective interior cavity housing a battery for powering the lighting sources associated therewith. The light emitting sources of each outer body portion are operatively associated with respective PCB's. A semi-annular lens is associated with the arcuately spaced apart light emitting sources at a distal end of each body portion.

A flexible latch is operatively associated with the first outer body portion for engaging a tab on the second outer body portion when the first and second body portion are moved into a closed position. Alternatively, magnetic or adhesive strips are operatively associated with the first and second outer body portions for maintaining the device in the closed positon. A switch is operatively associated with the recess portion in each outer body portion for activating the lighting sources associated therewith when the first and second body portion are moved into a closed position. It is envisioned that the lighting device would be automatically activated when an instrument is inserted into the device and the latch is closed around it, and it would be deactivating by removing the latch and/or the instrument.

Alternatively, a switch could be operatively associated with only one of the two outer body portions of the lighting device, and the other outer body portion could be connected thereto by a wire or sensor. It is also envisioned that a button could be provide on one of the two outer body portions, instead of a switch, so that when the lighting device is closed around an instrument, the light emitting sources would be activated. This could also be accomplished with an internal switch associated with the flexible latch, in which case the lighting device could detect when the body portions are latched shut and then automatically turn on.

In another embodiment of the subject invention, the lighting device includes a generally hemi-cylindrical outer body defining an interior cavity, an interior body enclosing the interior cavity of the outer body and defining a generally hemi-frusto-conical recess for accommodating a distal end portion of the surgical instrument, and a set of arcuately spaced apart light emitting source arranged at a distal end of the interior cavity of the outer body. A semi-annular lens is associated with the arcuately spaced apart light emitting sources at a distal end of the body portion.

There are a number of advantages to this embodiment of the invention. First, it can remove the bulk of the body of the lighting device from the line of sight of the surgeon when they look down the face of the electrosurgical instrument (typically they hold it and look down the face with the buttons). The second advantage to this embodiment is its open side, which can readily accommodate different geometries of instruments. For example, some instruments are sold with an integral smoke evacuation line, and this configuration of the lighting device could readily accommodate such a feature.

Preferably, radially outwardly projecting elastomeric wedges are mounted within the hemi-frusto-conical recess for frictionally, resiliently or in spring-loaded manner engaging the distal end portion of the surgical instrument. A battery is housed within the interior cavity for powering the light sources associated therewith when the device is activated. The light emitting source is operatively associated with a PCB. A switch is operatively associated with the recess portion for activating the light emitting sources associated therewith. It is envisioned that the elastomeric wedges could be spring loaded and designed to function both as a way to keep the instrument locked in place within the lighting device and as a way to activate the light if there is a switch or button underneath the wedges. It is also envisioned that the lighting device would be automatically activated when an instrument is inserted into the device, and it would be deactivating by removing the instrument therefrom.

In another embodiment of the subject invention, the lighting device includes a a generally cylindrical outer body portion including an interior body portion defining a generally frusto-conical recess for accommodating a distal end portion of the surgical instrument. The outer body portion has a set of circumferentially spaced apart light emitting sources at a distal end thereof.

The lighting device further includes a manually actuated engagement assembly for releasably engaging the distal end portion of the surgical instrument upon reception within the generally frusto-conical recess. The manually actuated engagement assembly includes a pair of spring-loaded and radially inwardly biased diametrically opposed annular engagement bands each having a plurality of engagement teeth for releasably engaging the distal end portion of the surgical instrument. Each of the opposed annular engagement bands has a compressible tab associated therewith for releasing the distal end portion of the surgical instrument when they are compressed radially inwardly.

Alternatively, the diametrically opposed annular engagement bands each have an engagement member for releasably engaging the distal end portion of the surgical instrument. The engagement member could be made from an elastomeric, plastic or metal material. Those skilled in the art will readily appreciate that the conformable nature of the engagement assembly of this embodiment will facilitate the use of the lighting device with instruments of varying size and/or geometry. It is envisioned that the lighting device would be automatically activated when an instrument is received within the engagement assembly and/or deactivating by removing the instrument therefrom.

It is also envisioned that a light source and/or a surgical instrument could be provided with one or more adhesive stickers for adhering the light source to the instrument.

The subject invention is also directed to a kit that includes a handheld surgical instrument; a battery powered lighting device for attachment to the handheld surgical instrument; and a packaging enclosure containing the surgical instrument and the lighting device. Preferably, the handheld surgical instrument is an electrosurgical pencil.

These and other features of the subject invention will become more readily apparent to those having ordinary skill in the art to which the subject invention appertains from the detailed description of the preferred embodiments taken in conjunction with the following brief description of the drawings.

BRIEF DESCRIPTION OF THE DRAWINGS

So that those skilled in the art will readily understand how to make and use the subject invention without undue experimentation, preferred embodiments thereof will be described in detail herein below with reference to the figures wherein:

FIG. 3 is a first side elevational view of the lighting device engaged on the distal end portion of the surgical instrument;

FIG. 4 is a second side elevational view of the lighting device engaged on the distal end portion of the surgical instrument;

FIG. 5 is a cross-sectional view taken along line B-B of FIG. 3;

FIG. 6 is a front end view of the lighting device engaged on the distal end portion of the surgical instrument;

FIG. 7 is an enlarged localized view of the latch for securing the subassemblies of the lighting device in a closed position;

FIG. 8 is a first side elevational view of the lighting device is a closed position;

FIG. 9 is a second side elevational view of perspective view of the lighting device is a closed position;

FIG. 10 is a rear end view of the lighting device is a closed position;

FIG. 11 is a perspective view of the lighting device is a closed position;

FIG. 42 is a top plan view of the lighting device and surgical instrument shown in FIG. 41;

FIG. 43 is a side elevational view of the lighting device and surgical instrument shown in FIG. 41;

FIG. 44 is a cross sectional view taken along line F-F of FIG. 43;

FIG. 45 is a front end view of the lighting device and surgical instrument shown in FIG. 41;

FIG. 46 is an enlarged localized view taken from FIG. 44;

DETAILED DESCRIPTION OF THE PREFERRED EMBODIMENTS

Figure 1:
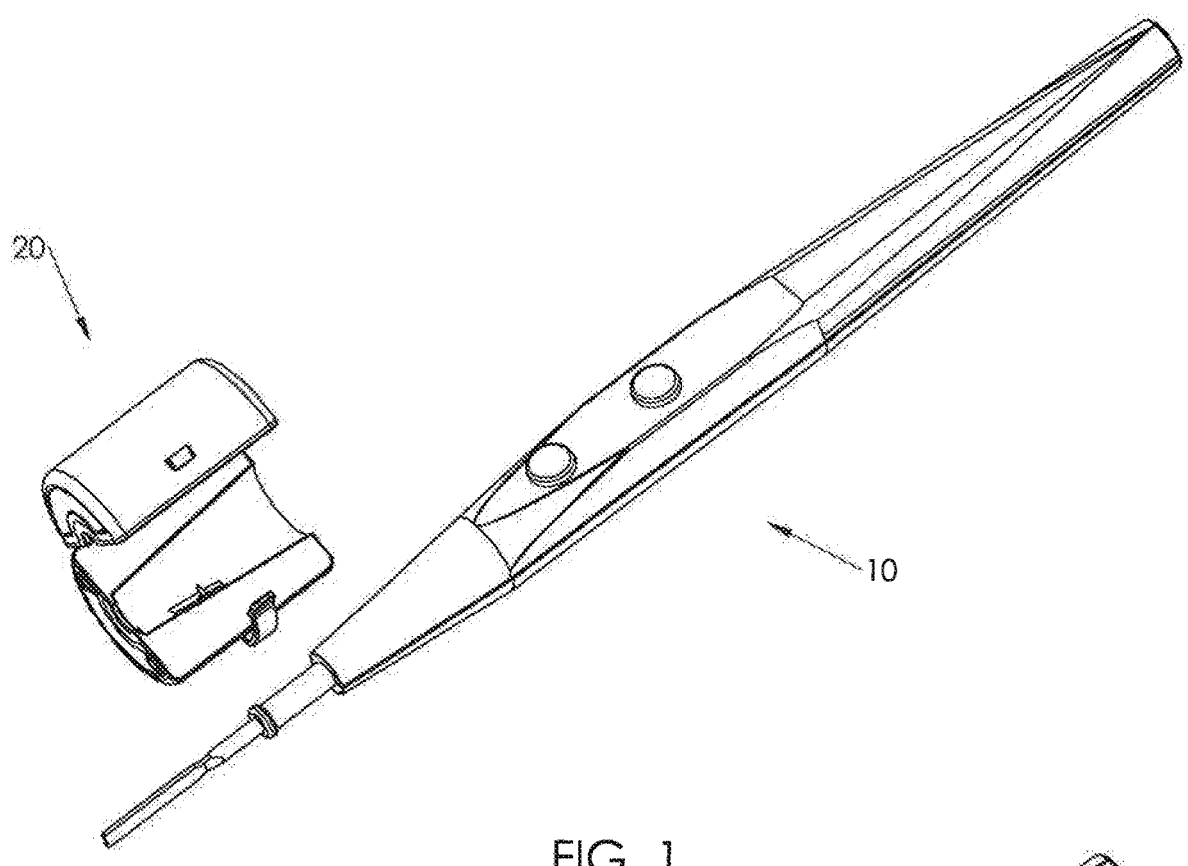
FIG. 1 is a perspective view of a first embodiment of the lighting device which includes two generally U-shaped sub-assemblies that are hingedly connected to one another, wherein the sub-assemblies are shown in an open position to receive the distal end portion of the surgical instrument.

Referring now to the drawings wherein like reference numerals identify similar structural elements of the various embodiments of the subject invention, there is illustrated in FIGS. 1-21, a cordless, battery powered lighting device, indicated generally by the reference numeral 20, that is removably installed on a distal end portion of an elongated handheld electrosurgical instrument 10, such as a BOVIE® pencil, which is manufactured and sold by Bovie Medical Corporation. In use, once the lighting device 20 is installed on the distal end portion of the electrosurgical instrument 10, an annulus of light automatically and simultaneously projects from the distal end of the lighting device 20, having an illumination axis centered along the longitudinal axis of the instrument 10.

As best seen in FIGS. 3-5, an elongated electrode blade 4 having a medially located flange 6 is operatively associated with an axial opening in the distal end portion 2 of the instrument 10. The electrode blade 4 can be attached to the instrument 10 before the lighting device 20 is installed on the distal end portion of the instrument 10 or after the lighting device 20 has been installed on the distal end portion of the instrument 10. Once installed, the electrode blade 4 will be located on the focal axis of the lighting device 20.

Referring to FIGS. 3-16, in the first embodiment of the subject invention, the lighting device 20 has two hingedly connected outer body portions 8' and 8". The first outer body portion 8' has a first interior body portion 32' defining a first recess portion for accommodating a distal end portion of the surgical instrument 10. In addition, the first outer body portion 8' has a first set of arcuately spaced apart LED light sources 36 operatively associated with a distal end thereof. The second outer body portion 8" has a second interior body portion 32" defining a second recess portion for accommodating the distal end portion of the surgical instrument 10. In addition, the second outer body portion 8" has a second set of arcuately spaced apart LED light sources 36 operatively associated with a distal end thereof. The LED light sources 36 are surface mounted or otherwise operatively associated with a PCB 16, as best seen in FIG. 14. These components may be blue LEDs, white LEDs, yellow LEDs, etc.

Figure 2:
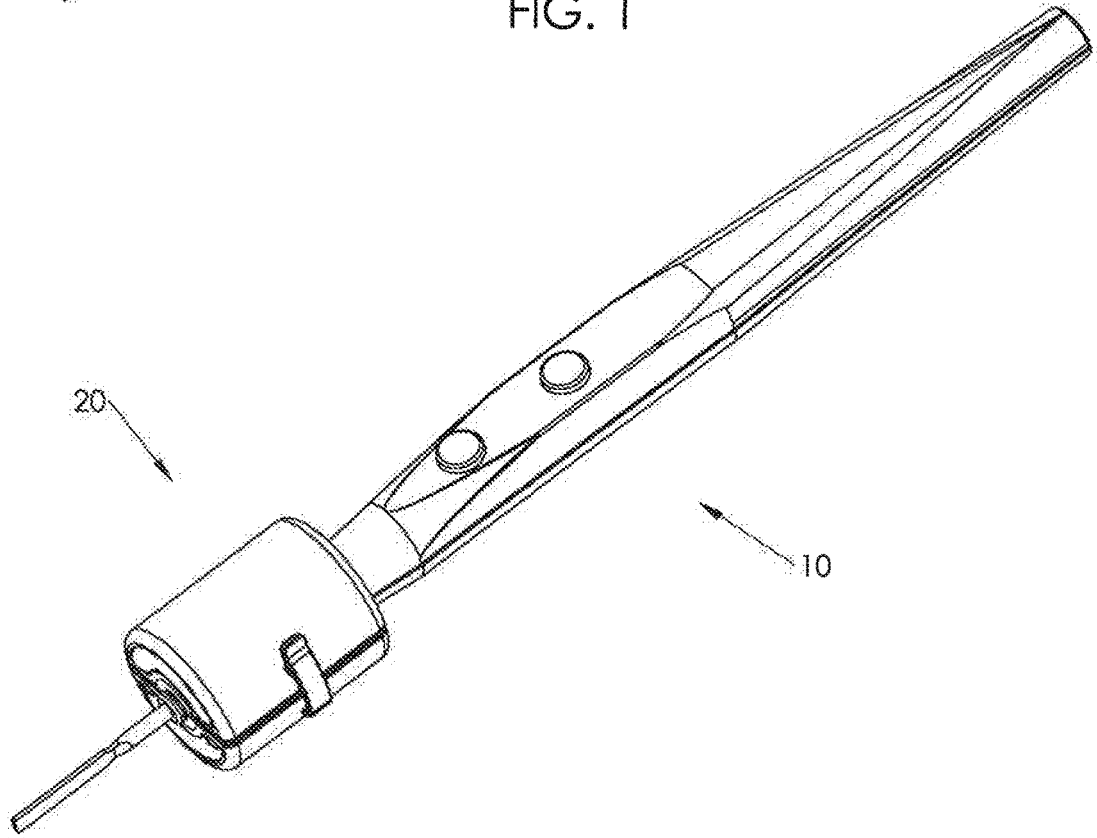
FIG. 2 is a perspective view of the lighting device in a closed position engaged on the distal end portion of the surgical instrument.
Figure 12:
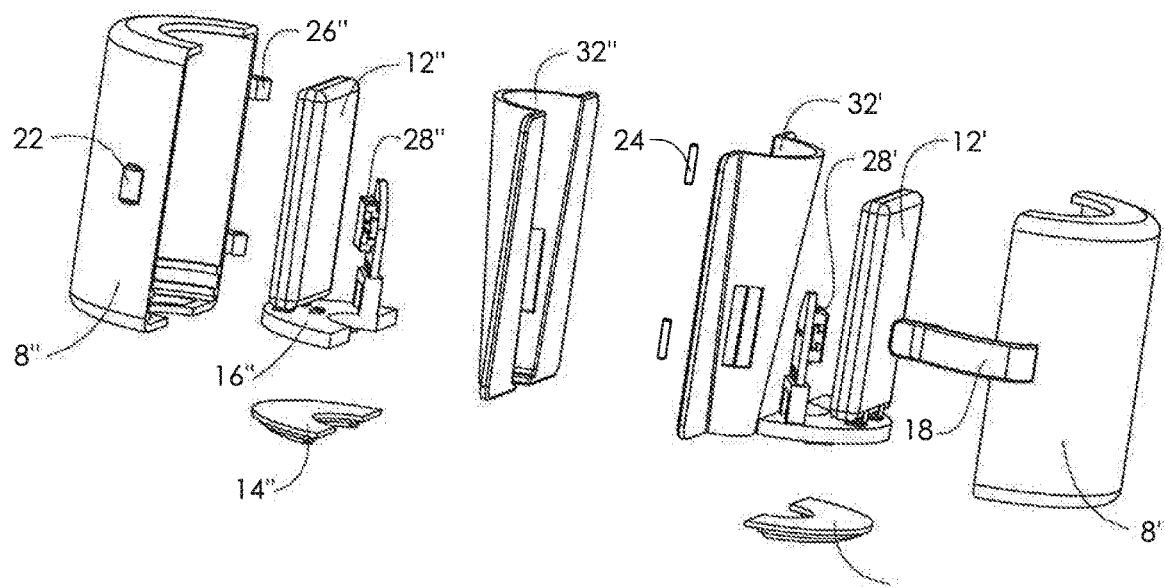
FIG. 12 is an exploded perspective view of the lighting device shown in FIG. 11.
Figure 16:
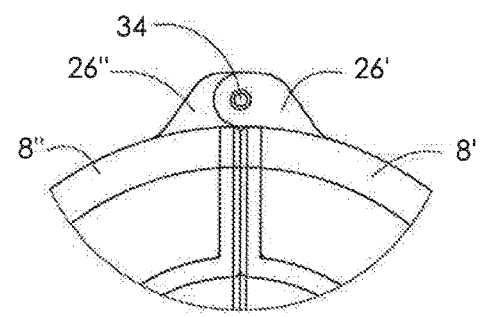
FIG. 16 is an enlarged localized view of the hinge taken from FIG. 10.
Figure 17:
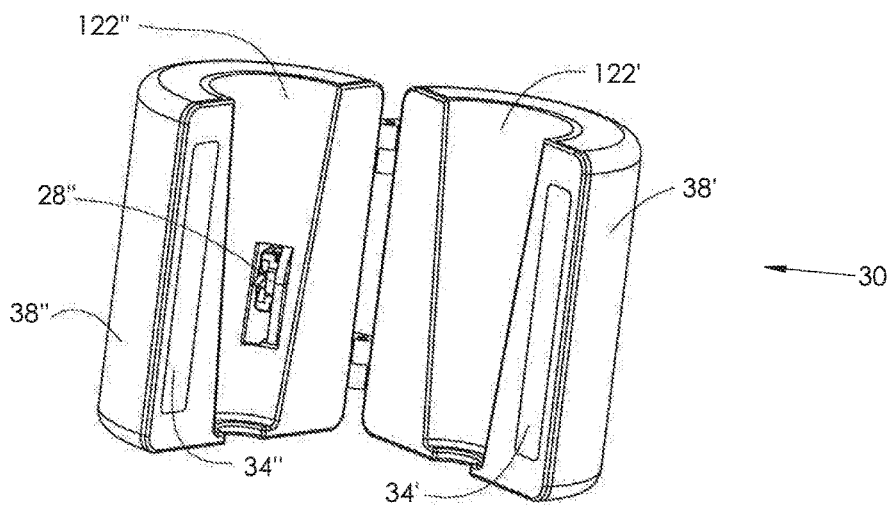
FIG. 17 is a perspective view of another version of the lighting device of FIG. 11 in an open position, which includes magnetic or adhesive strips.
Figure 18:
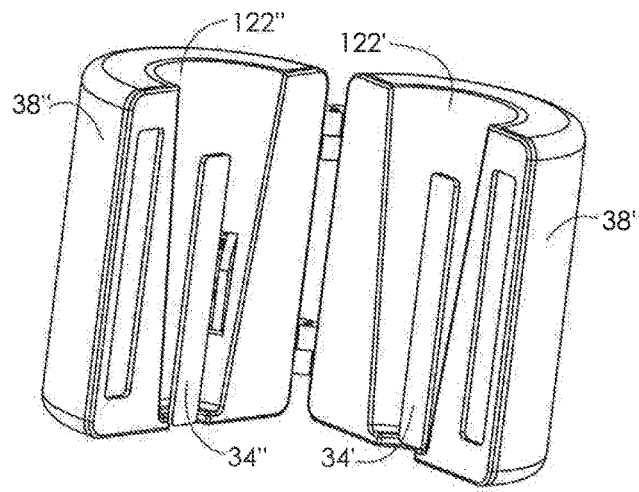
FIG. 18 is a perspective view of the lighting device of FIG. 17, with the magnetic or adhesive strips separated for ease of illustration.
Figure 19:
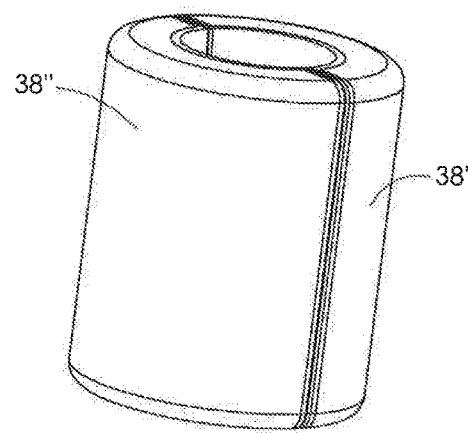
FIG. 19 is perspective view of the lighting device of FIG. 17 in a closed position.
Figure 20:
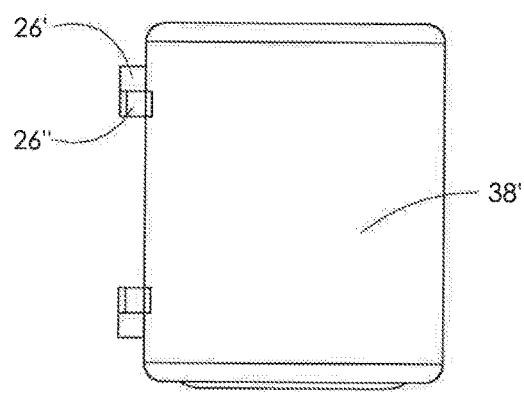
FIG. 20 is a side elevational view of the lighting device of FIG. 17 in a closed position.
Figure 21:
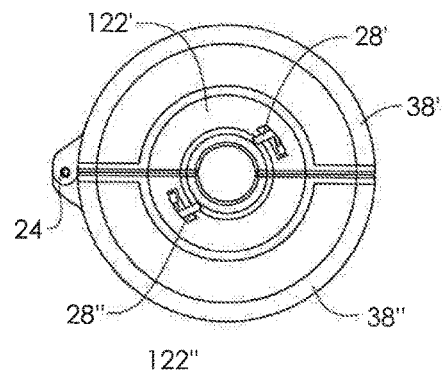
FIG. 21 is rear end view of the lighting device of FIG. 17 in a closed position.
Figure 22:
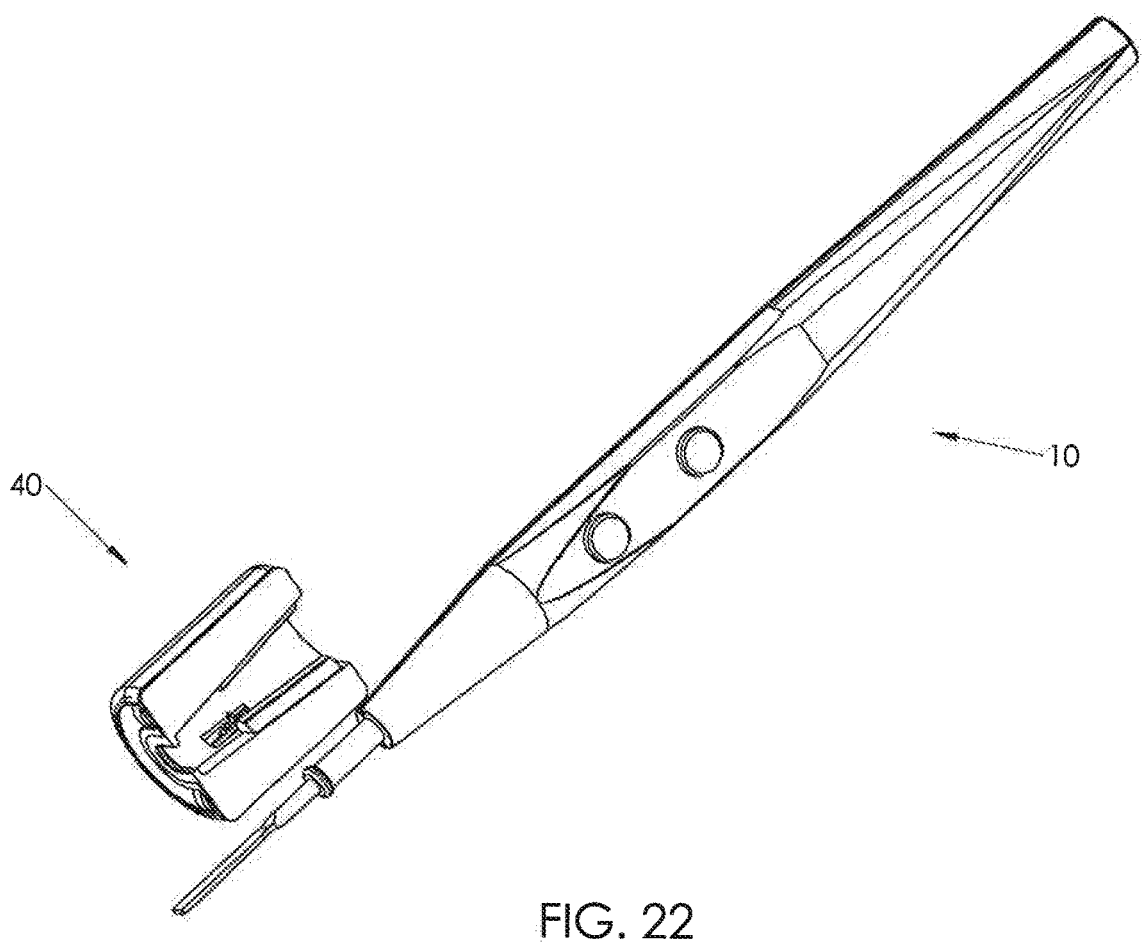
FIG. 22 is a perspective view of a second embodiment of the lighting device which includes a generally U-shaped body which includes radially inwardly projecting rubber wedged structures for engaging the distal end portion of the surgical instrument.
Figure 23:
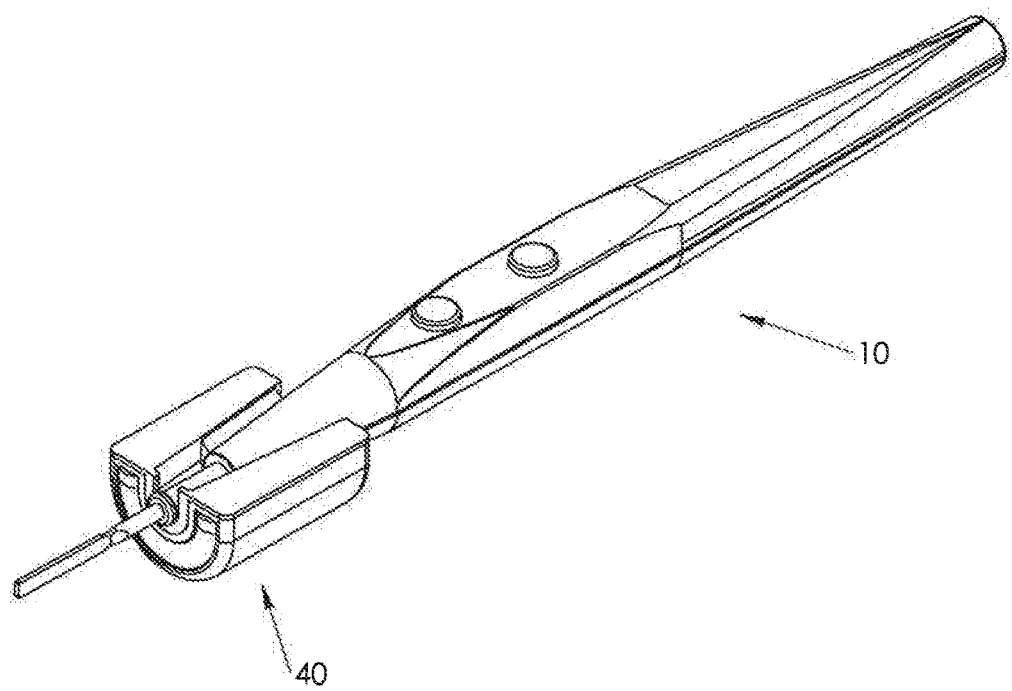
FIG. 23 is a perspective view of the lighting device shown in FIG. 22, engaged on the distal end portion of the surgical instrument.
Figure 24:
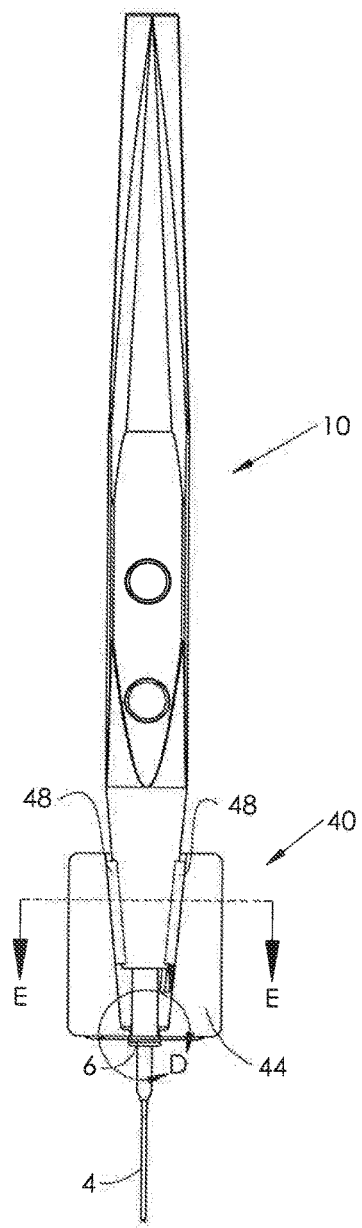
FIG. 24 is a top plan view of the lighting device and surgical instrument shown in FIG. 23.
Figure 25:
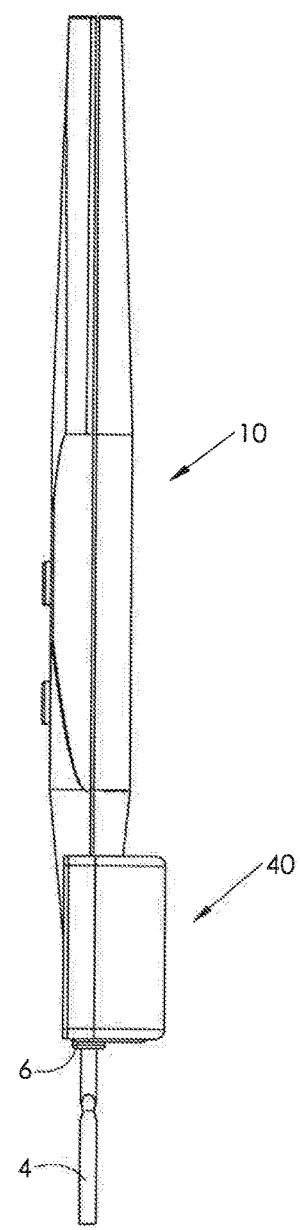
FIG. 25 is a side elevational view of the lighting device and surgical instrument shown in FIG. 23, which illustrates the advantage of allowing the surgeon to see down the face of the instrument without the lighting device blocking their line of sight.

The first and second body portions 8' and 8" of the lighting device 20 are hingedly connected to one another and configured for movement between an open position shown in FIG. 1 for receiving the distal end portion 2 of the surgical instrument 10 and a closed positon shown in FIG. 2 for engaging the distal end portion 2 of the surgical instrument 10. More particularly, as best seen in FIGS. 12 and 16, the first and second outer body portions 8' and 8" have respective axially spaced apart hinge structures 26' and 26" for accommodating a pair of hinge pins 24. Preferably, the first and second outer body portions 8' and 8" each have a generally hemi-cylindrical configuration, and the first and second inner body portions 32' and 32" each have respective recess portions that have a generally hemi-frusto-conical configuration.

Figure 13:
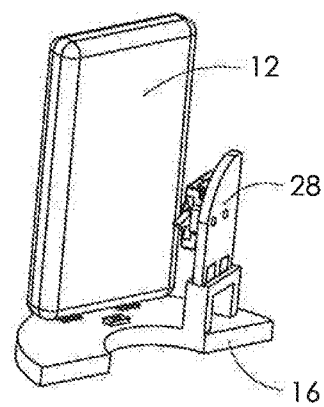
FIG. 13 is a first perspective view of the PC board assembly and battery.
Figure 14:
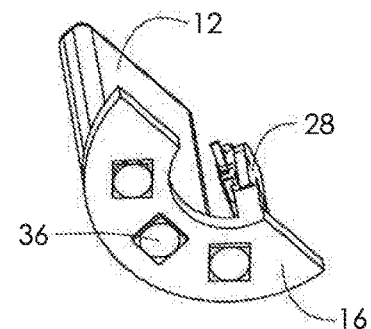
FIG. 14 is a second perspective view of the PC board assembly and battery.
Figure 15:
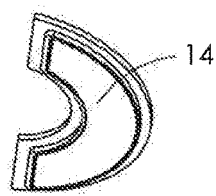
FIG. 15 is a perspective view of the lens.

The first and second outer body portions 8' and 8" each define a respective interior cavity that houses a battery 12' and 12" for powering the LED lighting sources 36 associated therewith, as best seen in FIGS. 12-14. It is envisioned that the batteries 12' and 12" could be rechargeable or replaceable. As noted above, the LED lighting sources 36 of each outer body portion 8' and 8" are operatively associated with respective PCB's 16' and 16". The PCBs 16' and 16" can be rigid or flexible. A semi-annular lens 14' and 14" is associated with the arcuately spaced apart LED light sources 36 at the distal end of each body portion 8' and 8", which is best seen in FIGS. 12 and 15.

It is envisioned that the LED light sources 36 could be adapted and configured to produce visible light or UV light, including UV-C light. The use of UV-C light sources is intended to treat or prophylax against infectious organisms without requiring the surgeon to pause and specifically treat the tissues in such a manner. Rather, the surgeon may continue to utilize a device such as the electrocautery device 10 while the cordless, removably attached UV-C lighting device is actively irradiating the same tissues. UV-C radiation has been shown to be more lethal against susceptible organisms with increasing exposure, though increasing distance from the site decreases the effectiveness. With the fixed distance of the light within this device as well as the benefit of concomitant treatment while the surgeon is working, the UV-C light device proves to be a novel method of treatment. In addition, it is envisioned that the device may be configured to deliver concomitant visible lighting to improve illumination alongside UV-C light within the same device.

It is also envisioned that a camera could be operatively associated with one of the PCBs 16' and 16", and that camera could be a NIR camera for illuminating contrast dye or detecting tissue contrast. Associated control circuitry would be provided on the PCB or elsewhere within the lighting device.

A mechanical switch 28' and 28" is operatively associated with the recess portion in each outer body portion 8' and 8" for activating the lighting sources 36 associated therewith when the first and second body portion 8' and 8" are moved into a closed position around the distal end portion of the instrument 10, as shown for example in FIG. 12. Other types of mechanical switching mechanism and/or sensors could be employed, on one or both of the body portions of the lighting device.

As best seen in FIGS. 6-11, a flexible latch 18 is operatively associated with the first outer body portion 8' for engaging a rigid tab or tooth 22 on the second outer body portion 8" when the first and second outer body portions 8' and 8" are moved into the closed position of FIG. 2. This will lock the two body portions together in a closed position. Alternatively, in the embodiment of FIGS. 17-21, elongated magnetic strips 34' and 34" are operatively associated with the first and second outer body portions 8' and 8", respectively, for maintaining the lighting device 20 in a closed positon.

Figure 32:
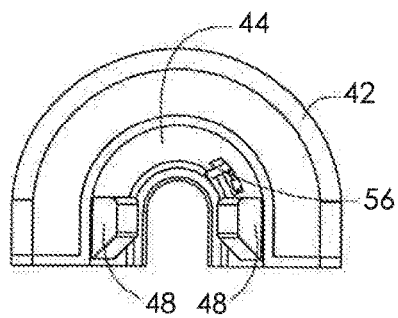
FIG. 32 is a rear end view of the lighting device shown in FIG. 22.

Referring now to FIGS. 22-39, there is illustrated another embodiment of the cordless, battery powered lighting device of the subject invention, which is designated generally by reference numeral 40. The lighting device 40 includes a generally hemi-cylindrical or U-shaped outer body 42 that defines an interior cavity (see FIGS. 28 and 32), an interior body 44 enclosing the interior cavity of the outer body 42 and defining a generally hemi-frusto-conical recess for accommodating a distal end portion of the surgical instrument 10, as shown in FIGS. 24-28.

Figure 33:
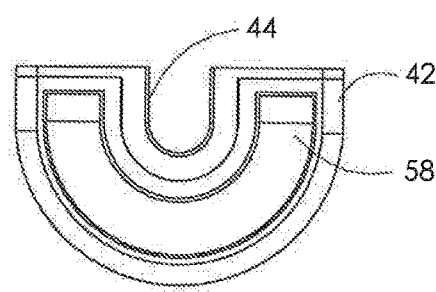
FIG. 33 is a front end view of the lighting device shown in FIG. 22.
Figure 35:
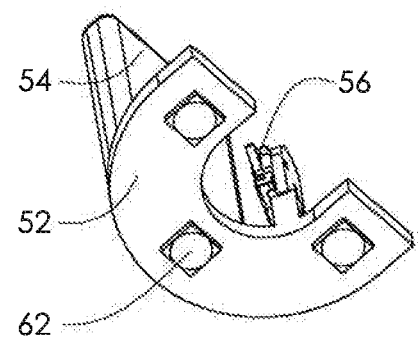
FIG. 35 is a second perspective view of the PC board assembly and battery of the lighting device shown in FIG. 29.
Figure 36:
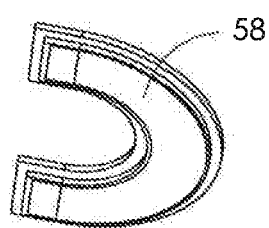
FIG. 36 is a perspective view of the lens of the lighting device shown in FIG. 29.
Figure 37:
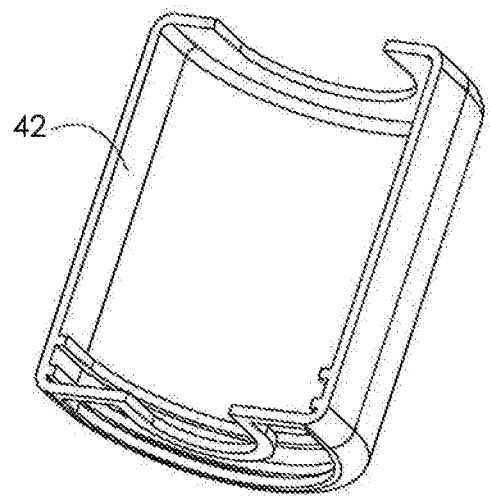
FIG. 37 is a perspective view of the outer body portion of the lighting device shown in FIG. 29.
Figure 38:
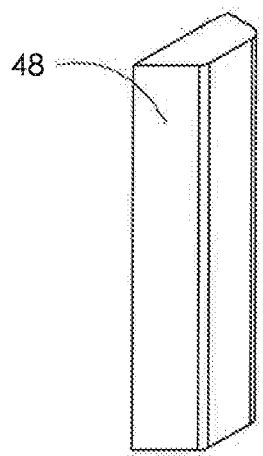
FIG. 38 is an enlarged perspective view of an elastomeric wedge member of the lighting device shown in FIG. 29.
Figure 39:
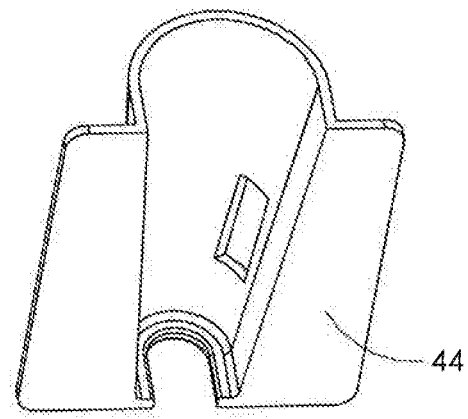
FIG. 39 is a perspective view of the inner body portion of the lighting device shown in FIG. 29.
Figure 40:
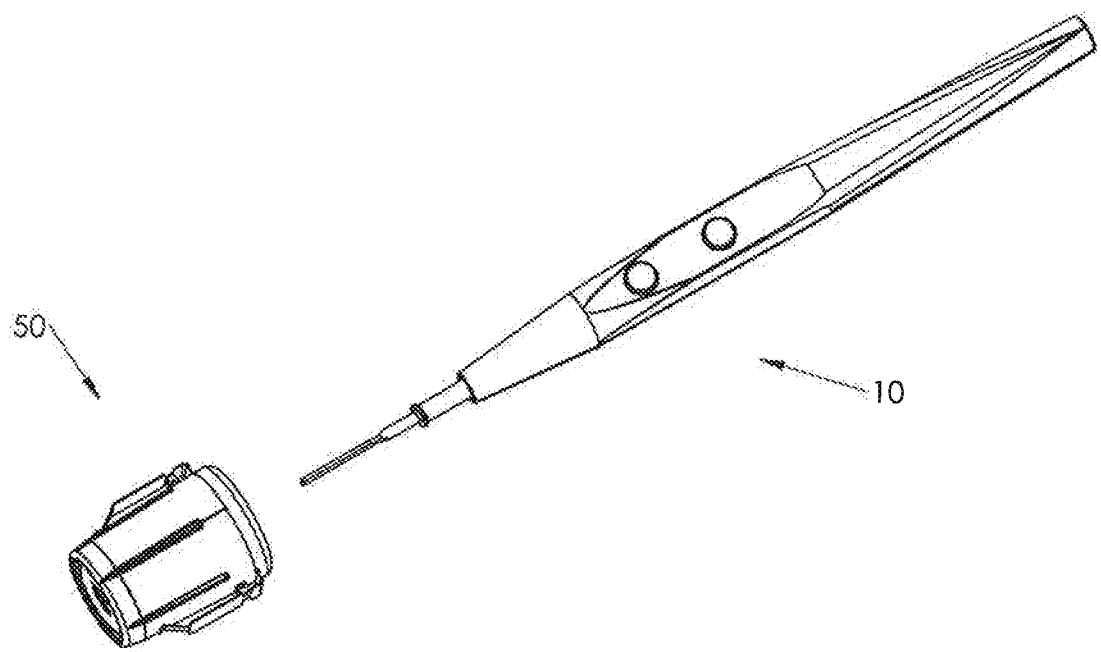
FIG. 40 is a perspective view of another lighting device and surgical instrument, wherein the lighting device includes a manually actuated latch assembly for engaging the lighting device on the distal end portion of the surgical instrument.
Figure 41:
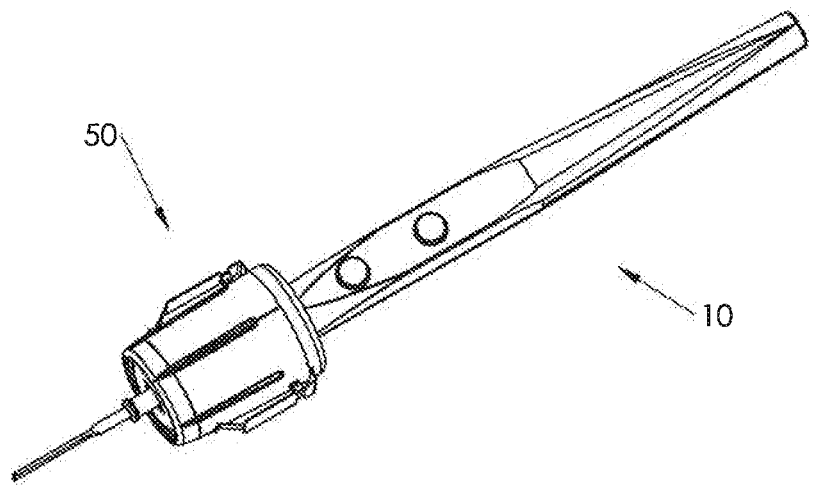
FIG. 41 is a perspective view of the lighting device shown in FIG. 40 installed on the distal end potion of the surgical instrument.
Figure 47:
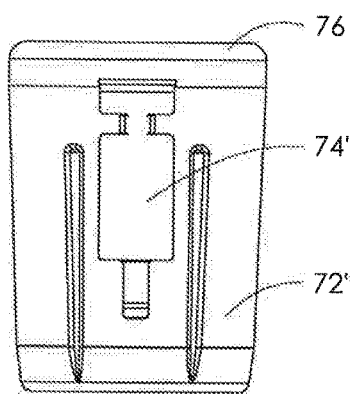
FIG. 47 is a first side elevational view of the lighting device of FIG. 40.
Figure 48:
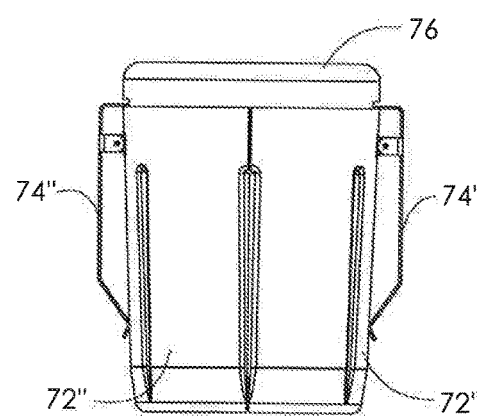
FIG. 48 is a second side elevational view of the lighting device of FIG. 40.
Figure 49:
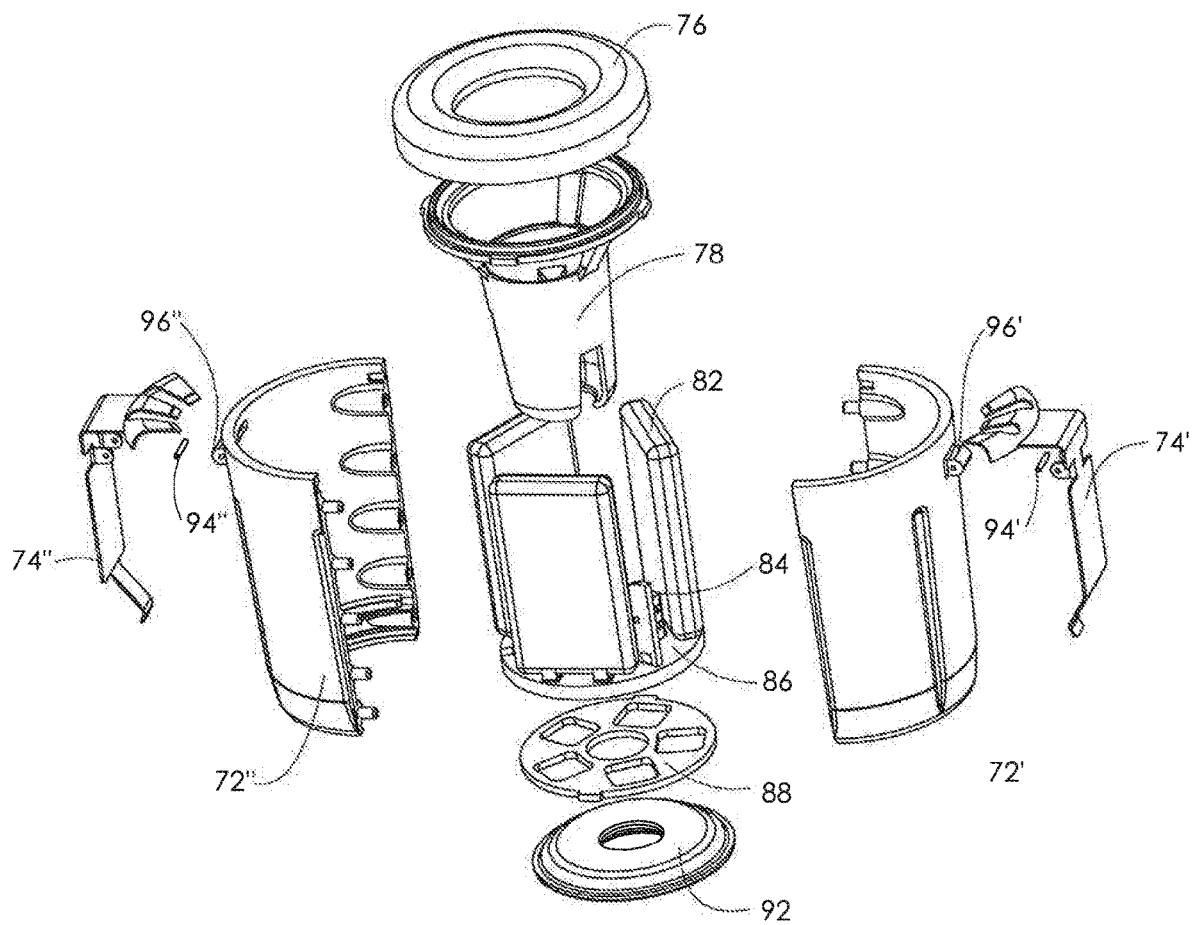
FIG. 49 is an exploded perspective view of the lighting device shown in FIG. 40.

As best seen in FIG. 35, a set of arcuately spaced apart LED light source 62 are arranged at a distal end of the interior cavity of the outer body 42. A semi-annular lens 58, best seen in FIGS. 33 and 36, is associated with the arcuately spaced apart LED light sources 62 at a distal end of the body portion. Preferably, as best seen in FIGS. 28-32, a pair of radially outwardly projecting elastomeric wedges 48 (see FIGS. 38 and 39) are mounted within the hemi-frusto-conical recess of the inner body portion 44 for frictionally, resiliently or otherwise engaging in a spring-loaded manner the distal end portion of the surgical instrument 10.

Figure 29:
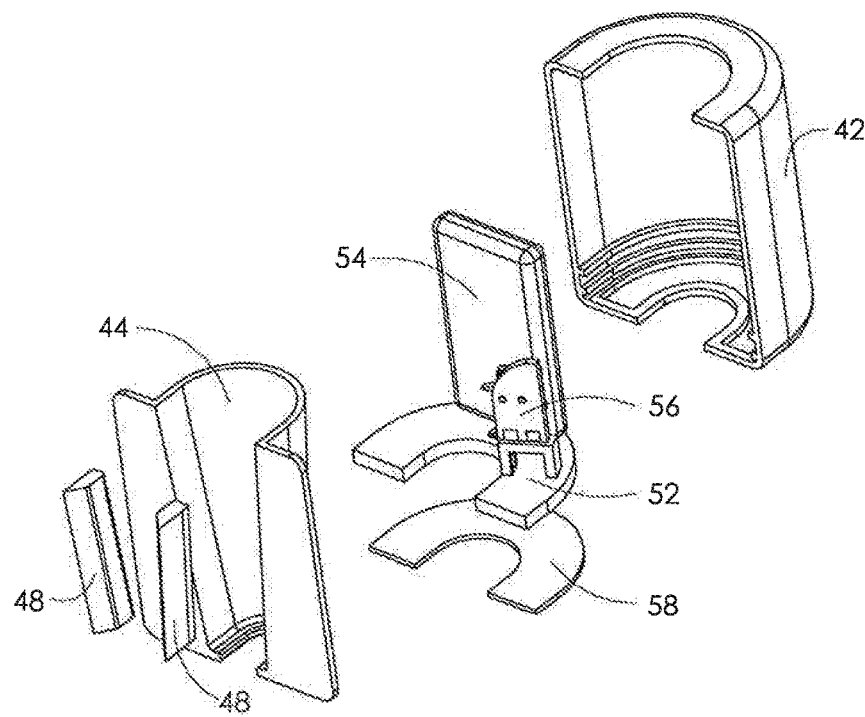
FIG. 29 is an exploded perspective view of the lighting device shown in FIG. 22.
Figure 30:
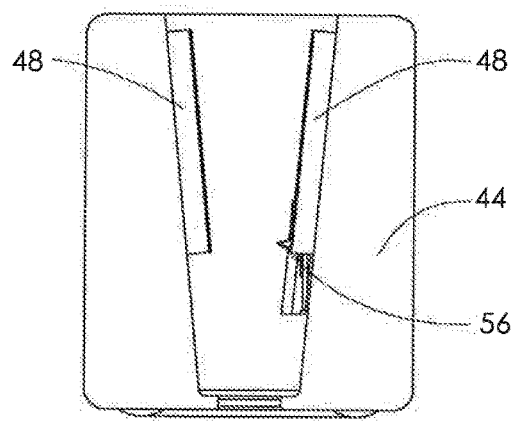
FIG. 30 is a top plan view of the lighting device shown in FIG. 22.
Figure 31:
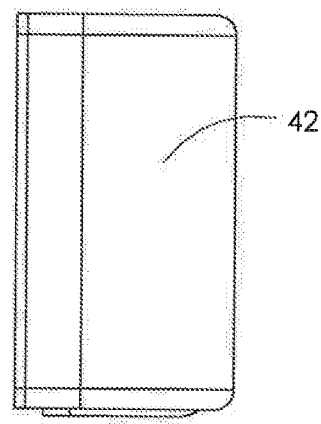
FIG. 31 is a side elevational view of the lighting device shown in FIG. 22.
Figure 34:
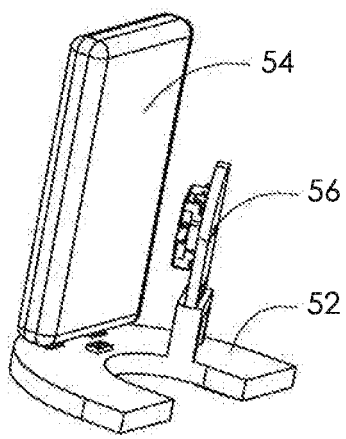
FIG. 34 is a first perspective view of the PC board assembly and battery of the lighting device shown in FIG. 29.

Referring to FIGS. 29 and 34-35, a battery 54 is housed within the interior cavity of the outer body 42 for powering the LED light sources 62 associated therewith, and the LED light sources 62 are operatively associated with a PCB 52.

A mechanical switch 56 is operatively associated with the recess portion of the inner body portion 44 for activating the light sources 62 associated therewith when the distal end portion of the instrument 10 is engaged therein.

Figure 26:
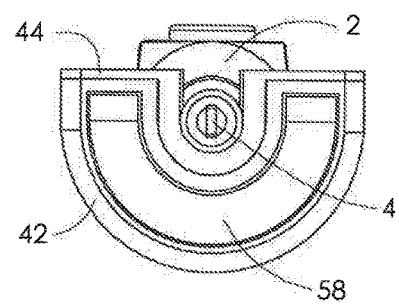
FIG. 26 is a front end view of the lighting device and surgical instrument shown in FIG. 23.
Figure 27:
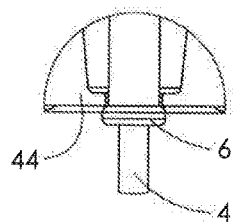
FIG. 27 is an enlarged localized view taken from FIG. 24.
Figure 28:
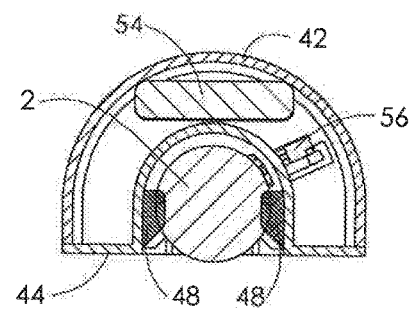
FIG. 28 is a cross sectional view taken along line E-E of FIG. 24.

Referring now to FIGS. 40-58, there is illustrated another embodiment of the cordless, battery powered lighting device of the subject invention, which is designated generally by reference numeral 50. The lighting device 50 includes a generally cylindrical outer body portion (72' and 72") that includes an interior body portion 78 defining a generally frusto-conical recess for accommodating a distal end portion 2 of the surgical instrument 10, as best seen in FIG. 44. The outer body portion (72' and 72") has a set of circumferentially spaced apart LED light sources mounted on a PCB board 86 at a distal end thereof. An annular lens 92 is associated with the circumferentially spaced apart LED light sources at a distal end of the body portion 72, as best seen in FIGS. 26 and 36. A spacer 88 is disposed between the light sources on the PCB 86 and the lens 92.

A plurality of batteries 82 are housed within the interior cavity of the outer body portion 72 for powering the LED light sources associated therewith, and the LED light sources are operatively associated with a PCB 86. A switch 84 is mounted on the PCB 86 and operatively associated with the recess portion of the inner body portion 78 for activating the light sources associated therewith.

The lighting device 50 further includes a manually actuated engagement assembly for releasably engaging the distal end portion of the surgical instrument 2 upon reception in the generally frusto-conical recess of the inner body portion 78. The manually actuated engagement assembly includes a pair of diametrically opposed compressible metal tabs 74' and 74" which have respective lower tab spring structures 102' and 102" and semi-annular sets of spaced apart engagement teeth 98 for releasably engaging the distal end portion of the surgical instrument 10. Each metal tab 74', 74" includes a respective integral hinge structure 104 for interacting with hinge structures 96' and 96" on the outer body portions (72' and 72") by way of hinge pins 94' and 94". A proximal end cap 76 encloses the engagement teeth 98 of metal tabs 74' and 74" within the outer body portion 72', 72".

Figure 50:
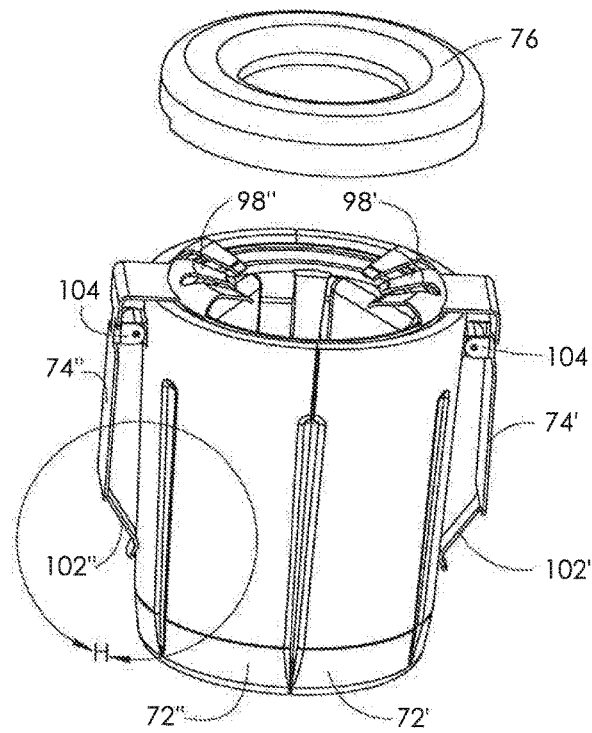
FIG. 50 is a perspective view of the lighting device shown in FIG. 40, with the end cap separated to illustrate the location of the engagement teeth when the latching tabs are not compressed.
Figure 51:
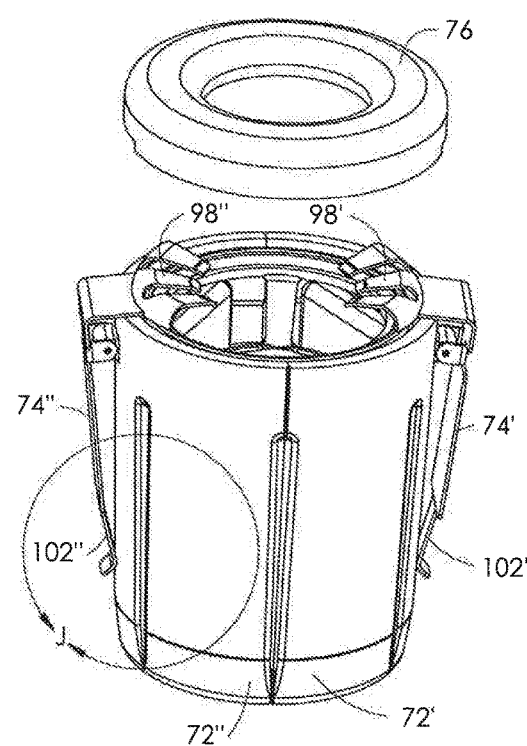
FIG. 51 is a perspective view of the lighting device shown in FIG. 40, with the end cap separated to illustrate the location of the engagement teeth when the latching tabs are compressed.
Figure 52:
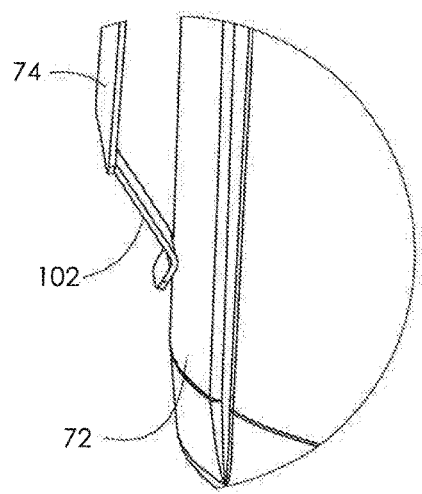
FIG. 52 is an enlarged localized view taken from FIG. 50.
Figure 53:
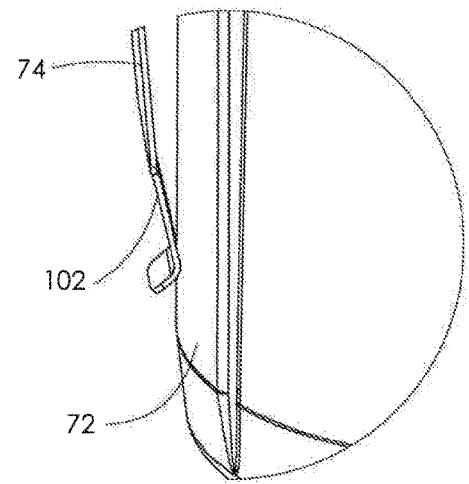
FIG. 53 is an enlarged localized view taken from FIG. 51.
Figure 54:
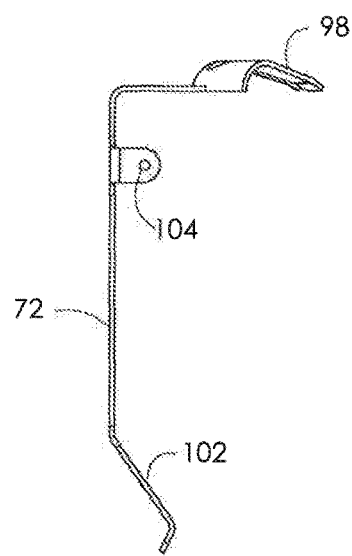
FIG. 54 is a side elevational view of a latching tab with engagement teeth.
Figure 55:
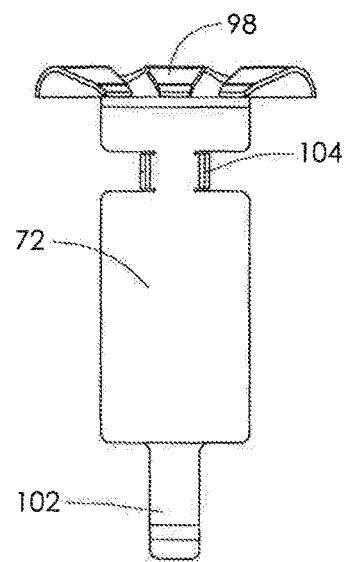
FIG. 55 is a front plan view of a latching tab with engagement teeth.
Figure 56:
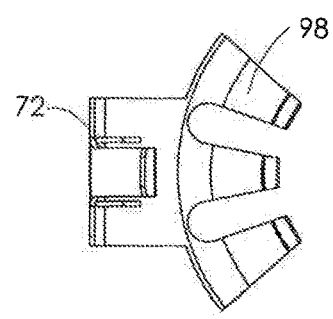
FIG. 56 is a top plan view of a latching tab with engagement teeth.
Figure 57:
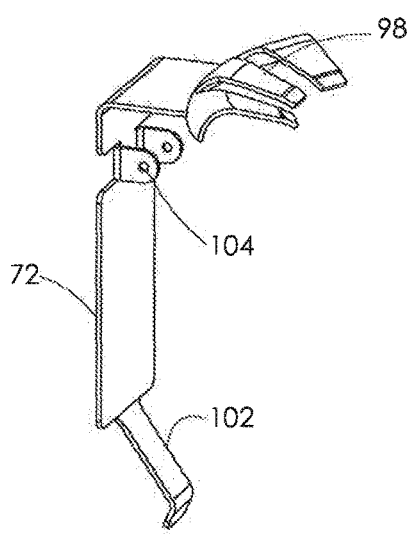
FIG. 57 is a perspective view of a latching tab with engagement teeth.

In use, the diametrically opposed metal tabs 74' and 74" are moved from an engaged, radially inwardly disposed position shown in FIGS. 50 and 52, to a disengaged, radially outwardly disposed position shown in FIGS. 51 and 53, by applying an inwardly directed force on tabs 74' and 74".

Figure 58:
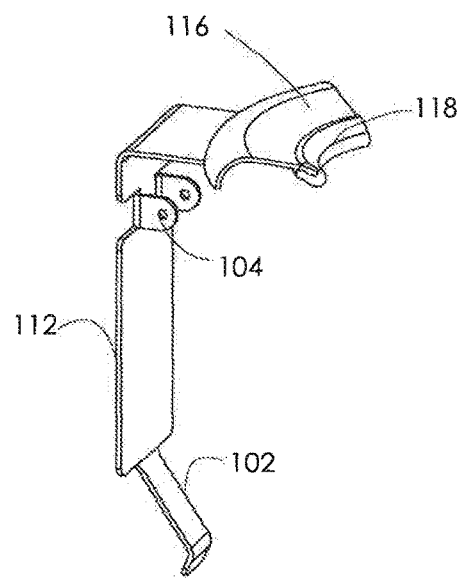
FIG. 58 is a perspective view of a latching tab with over molded elastomeric engagement structure.

In an alternative embodiment of the subject invention illustrated in FIG. 58, the manually actuated engagement assembly includes a pair of diametrically opposed metal or plastic tabs 112 each having a lower tab structure 102, a tab hinge structure 104 and an semi-annular upper tab structure 116 each having an over-molded elastomeric engagement member 118 for releasably engaging the distal end portion of the surgical instrument 10. This feature will allow the lighting device to be employed with surgical instruments of different size and/or geometry.

It is also envisioned and well within the scope of the subject disclosure that the lighting device could be provided with a mechanism that generates an audible or visible signal to that would indicate that the lighting device is properly engaged on the distal end portion of the surgical instrument. It is envisioned that the lighting device could also include an accelerometer or similar sensor that would turn on the LED light sources when the surgical device is moved from a horizontal to a vertical orientation and turn off the LED light sources when the surgical instrument is moved from a vertical orientation to a horizontal orientation.

It is also envisioned that the lighting device could be operatively associated with an inductive coupling that would be attached to the power cord of the surgical instrument so that when the surgical instrument is activated and current flows through the power cord, the LED light sources in the lighting device are activated, and when current is not flowing through the power cord, the light sources are not illuminated.

The subject invention is also directed to a kit that includes a handheld surgical instrument; a battery powered lighting device for attachment to the handheld surgical instrument; and a packaging enclosure containing the surgical instrument and the lighting device. Preferably, the handheld surgical instrument is an electrosurgical pencil. The lighting device contained in the packing enclosure could be either one of the lighting devices disclosed herein, or it could be the lighting device disclosed in commonly assigned U.S. Pat. No. 9,851,060, the disclosure of which has been previously incorporated by reference.

While the subject disclosure has been shown and described with reference to preferred embodiments, those skilled in the art will readily appreciate that changes or modifications may be made thereto without departing from the spirit or scope of the subject disclosure.

What is claimed is:

1. A lighting device for attachment to a handheld surgical instrument comprising:
    a) a first outer body portion including a first interior body portion defining a first recess portion for accommodating a distal end portion of the surgical instrument, wherein the first outer body portion has a first set of arcuately spaced apart LED light source at a distal end thereof;
    b) a second outer body portion including a second interior body portion defining a second recess portion for accommodating the distal end portion of the surgical instrument, wherein the second outer body portion has a second set of arcuately spaced apart LED light source at a distal end thereof, wherein the first and second outer body portions are hingedly connected to one another and configured for movement between an open position for receiving the distal end portion of the surgical instrument and a closed positon for engaging the distal end portion of the surgical instrument, wherein the first and second outer body portions define respective first and second interior cavities, and wherein the first and second interior body portions each have respective opposed planar wings that extend radially outwardly from the respective first and second recess portions thereof, and wherein the opposed planar wings of the first and second interior body portions enclose the respective first and second interior cavities of the first and second outer body portions.

2. A lighting device as recited in claim 1, wherein the first and second outer body portions each have a generally hemi-cylindrical configuration.

3. A lighting device as recited in claim 1, wherein the first and second recess portions have a generally hemi-frusto-conical configuration.

4. A lighting device as recited in claim 1, wherein the respective interior cavities of the first and second body portions are each housing a battery for powering the light sources associated therewith.

5. A lighting device as recited in claim 1, wherein the light source of each outer body portion is operatively associated with respective PCB's.

6. A lighting device as recited in claim 1, wherein the light source of each outer body portion is adapted and configured to produce visible light or UV light, including UV-C light.

7. A lighting device as recited in claim 1, wherein a flexible latch is operatively associated with the first outer body portion for engaging a tab on the second outer body portion when the first and second body portion are moved into a closed position.

8. A lighting device as recited in claim 1, wherein magnetic or adhesive strips are operatively associated with the first and second outer body portions for maintaining the device in the closed positon.

9. A lighting device as recited in claim 1, wherein a switch is operatively associated with the recess portion in each outer body portion for activating the light source associated therewith when the first and second body portion are moved into a closed position.

10. A lighting device as recited in claim 1, wherein a semi-annular lens is associated with the set of arcuately spaced apart light source at a distal end of each body portion.

11. A lighting device for attachment to a handheld surgical instrument comprising:
   a) a generally hemi-cylindrical outer body defining an interior cavity having a proximal end and a distal end;
   b) an interior body enclosing the interior cavity of the outer body and defining a generally hemi-frusto-conical recess for accommodating a distal end portion of the surgical instrument, wherein the hemi-frusto-conical recess has opposed side edges that taper radially inwardly from the proximal end of the outer body toward the distal end of the outer body, and wherein a planar wing extends radially outwardly from each opposed side edge of the hemi-frusto-conical recess to enclose the interior cavity of the outer body; and
   c) a set of arcuately spaced apart light source arranged at a distal end of the interior cavity of the outer body.

12. A lighting device as recited in claim 11, wherein elastomeric wedges are mounted within the hemi-frusto-conical recess for resiliently engaging the distal end portion of the surgical instrument.

13. A lighting device as recited in claim 11, wherein a battery is housed within the interior cavity for powering the light source associated therewith.

14. A lighting device as recited in claim 11, wherein the light source is operatively associated with a PCB.

15. A lighting device as recited in claim 11, wherein the light source is adapted and configured to produce visible light or UV light, including UV-C light.

16. A lighting device as recited in claim 11, wherein a switch is operatively associated with the recess for activating the light source associated therewith.

17. A lighting device as recited in claim 11, wherein a semi-annular lens is associated with the set of arcuately spaced apart light source at a distal end of the outer body.

* * * * *